(12) United States Patent
Theoharides (10) Patent No.: US 9,176,146 B2
(45) Date of Patent: *Nov. 3, 2015

(54) METHODS OF TREATING AUTISM SPECTRUM DISORDERS AND COMPOSITIONS FOR SAME

(75) Inventor: Theoharis C. Theoharides, Brookline, MA (US)

(73) Assignee: Theta Biomedical Consulting & Development Co., Inc., Brookline, MA (US)

( * ) Notice: Subject to any disclaimer, the term of this patent is extended or adjusted under 35 U.S.C. 154(b) by 234 days.

This patent is subject to a terminal disclaimer.

(21) Appl. No.: 12/534,571

(22) Filed: Aug. 3, 2009

(65) Prior Publication Data

US 2011/0027397 A1 Feb. 3, 2011

(51) Int. Cl.
| | | |
|---|---|---|
| A61K 31/451 | (2006.01) | |
| A61K 31/352 | (2006.01) | |
| A61K 31/4545 | (2006.01) | |
| A61K 31/495 | (2006.01) | |
| A61K 31/519 | (2006.01) | |
| A61K 31/55 | (2006.01) | |
| A61K 36/63 | (2006.01) | |
| G01N 33/68 | (2006.01) | |
| A61K 31/00 | (2006.01) | |
| A61K 45/06 | (2006.01) | |

(52) U.S. Cl.
CPC ............ *G01N 33/6893* (2013.01); *A61K 31/00* (2013.01); *A61K 31/352* (2013.01); *A61K 31/451* (2013.01); *A61K 31/4545* (2013.01); *A61K 31/495* (2013.01); *A61K 31/519* (2013.01); *A61K 31/55* (2013.01); *A61K 36/63* (2013.01); *A61K 45/06* (2013.01); *G01N 2333/5412* (2013.01); *G01N 2800/30* (2013.01)

(58) Field of Classification Search
CPC ............ A61K 31/352; A61K 2300/00; A61K 31/4545; A61K 31/495; A61K 31/519; A61K 31/55; A61K 36/63
See application file for complete search history.

(56) References Cited

U.S. PATENT DOCUMENTS

| | | |
|---|---|---|
| 5,223,257 A | 6/1993 | Arora |
| 5,250,529 A | 10/1993 | Theoharides |
| 5,260,335 A | 11/1993 | Wagner et al. |
| 5,648,355 A | 7/1997 | Theoharides |
| 5,795,905 A | 8/1998 | McCarthy et al. |
| 5,804,594 A | 9/1998 | Murad |
| 5,821,259 A | 10/1998 | Theoharides |
| 5,855,884 A | 1/1999 | Theoharides |
| 5,876,744 A | 3/1999 | Della Valle et al. |
| 5,972,999 A | 10/1999 | Murad |
| 5,980,865 A | 11/1999 | Ahmed |
| 5,994,357 A | 11/1999 | Theoharides |
| 6,020,305 A | 2/2000 | Theoharides |
| 6,136,795 A | 10/2000 | Florio |
| 6,162,787 A | 12/2000 | Sorgente et al. |
| 6,211,195 B1 | 4/2001 | Webb et al. |
| 6,475,534 B2 * | 11/2002 | Xie et al. |
| 6,586,448 B1 | 7/2003 | DeNinno et al. |
| 6,689,748 B1 | 2/2004 | Theoharides |
| 6,765,008 B1 | 7/2004 | Chen |
| 7,700,138 B2 * | 4/2010 | Murdock et al. |
| 7,799,354 B2 * | 9/2010 | Murdock et al. |
| 2001/0000340 A1 | 4/2001 | Chen et al. |
| 2002/0146393 A1 | 10/2002 | Bell et al. |
| 2003/0194719 A1 | 10/2003 | Waring et al. |
| 2004/0213829 A1 | 10/2004 | Coleman et al. |
| 2005/0220909 A1 | 10/2005 | Theoharides |
| 2006/0013905 A1 | 1/2006 | Tehoharides |
| 2006/0179492 A1 | 8/2006 | Feifel |
| 2006/0210551 A1 | 9/2006 | Lindsberg et al. |
| 2007/0077317 A1 | 4/2007 | Theoharides |
| 2007/0141187 A1 | 6/2007 | Theoharides |
| 2008/0160007 A1 | 7/2008 | Powell |
| 2009/0156668 A1 | 6/2009 | Vitolo et al. |

FOREIGN PATENT DOCUMENTS

| | | |
|---|---|---|
| EP | 0426479 | 5/1991 |
| GB | 2105193 | 9/1984 |
| WO | WO-9833494 | 8/1998 |
| WO | WO-0078320 | 12/2000 |
| WO | WO 2008011364 A2 * | 1/2008 |
| WO | WO-2008011364 A2 | 1/2008 |
| WO | WO-2010062681 A2 | 6/2010 |

OTHER PUBLICATIONS

Niederhofer. Phytother Res. (Mar. 9, 2009); 23: 1645-1646. First preliminary results of an observation of Gingko biloba treating patients with autistic disorder.*

Oyama, Y et al. Brain Research; vol. 635, Issues 1-2, Jan. 28, 1994, pp. 125-129. Myricetin and quercetin, the flavonoid constituents of Ginkgo biloba extract, greatly reduce oxidative metabolism.*

Bastianetto, S et al. J of Neurochemistry (2000); 74(6):2268-2277. The Gingko biloba extract (EGb 761) protects and rescues hippocampal cells against nitric oxide-induced toxicity: Involvemtn of its flavonoid constituents and protein Kinase C.*

Kumar, A et al. J of Medicinal Food (2008); 11(3): 469-473. Quercetin protects against acute immobilization stress-induced behaviors and biochemical alterations in mice.*

Chauhan, A et al. Pathophysiology (2006); 13: 171-181. Oxidative stress in autism.*

Sharma, V et al. Brain Research (2007); 73: 55-63. Modulation of interleukin 1-1β mediated inflammatory response in human astrocytes by flavonoids: Implications in neuroprotection.*

(Continued)

*Primary Examiner* — Michele Flood
(74) *Attorney, Agent, or Firm* — Wilmer Cutler Pickering Hale and Dorr LLP (57) ABSTRACT

Disclosed are compositions that inhibit brain blood vessel leakage, compositions for treating autism spectrum disorders, methods of treating autism spectrum disorders, and methods of screening for an autism spectrum disorder.

15 Claims, 3 Drawing Sheets

(56) References Cited

OTHER PUBLICATIONS

Akhondzadeh, S. et al., "Cyprohetadine in the treatment of autistic disorder: a double-blind placebo-controlled trial," J. of Clincal Pharmacy and Therapeutics, vol. 29: 145-150 (2004).

Chauhan, A. et al., "Oxidative stress in autism,", vol. 13: 171-181 (2006).

Kumar, A. et al., "Quercetin protects against acute immobilzation stress-induced behaviors and biochemical alterations in mice," J. of Medicinal Food, vol. 11(3): 469-473 (2008).

Sharma, V. et al., "Modulation of interleukin 1-1β mediated inflammatory response in human astrocytes by flavonoids: Implications in neuroprotection," Brain Research, vol. 73: 55-63 (2007).

Anonymous, "Autism LutiMax Reversed 2.short" Youtube video: http://www.youtube.com/watch?v-iaufJ00av, uploaded on Dec. 29, 2008 (4 pages).

Anonymous, "Autism Reversed by Carlee # 1", Youtube video: http://www.youtube.com/watch?v=K-r7G20h_1, uploaded on Dec. 27, 2008 (4 pages).

Anonymous, "Lutimax-Luteolin, Lutimax," www.lutimax.com, retrieved on Nov. 21, 2012 (XP-002687627) (1 page).

Anonymous, "Lutimax-Luteolin, Lutimax," www.lutimax.com, retrieved on Nov. 21, 2012 (XP-002687628) (1 page).

Ellis, S., "Help for Autism with a supplement," http://www.kylestreehouse.org, dated Feb. 14, 2009 (2 pages).

European Search Report issued for EP09848121, dated Nov. 21, 2012 (17 pages).

Gudarzi, S-S, et al., "Cyproheptadine in treatment of autism," Eur. Psychiatry, vol. 17: 230-231 (2002).

Jang, S. et al., "Luteolin reduces IL-6 production in microglia by inhibiting JNK phosphorylation and activation of AP-1," PNAS, vol. 105(21): 7534-7539 (May 27, 2008).

Li, X. et al., "Elevated immune response in the brain of autistic patients." J. Neuroimmunology, vol. 27: 111-116 (2009).

Smith, S.E.P., et al., "Maternal Immune Activation Alters Fetal Brain Development through Interleukin-6," J. Neuroscience, vol. 27(4): 10695-10702 (2007).

Diagnostic and Statiscal Manual of Mental Disorders (DSM-IV-TR) (4th ed., text rev.).

Smith, M.A. et al., "Oxidative stress in Alzheimer's disease," Biochimica et Biophysica Acta, vol. 1502, pp. 139-144 (2000).

International Search Report and Written Opinion, International Patent Application No. PCT/US08/86059, mailed Jan. 26, 2009 (2 pages).

Russell, A.L. and McCarty, M.F. "Glucosamine for migraine prophylaxis?" Medical Hypotheses, 55(3): 195-198 (2000).

Matsuda, K. et al., "Inhibitory Effects of Sialic-Acid- or N-Acetylglucosamine-Specific Lectins on Histamine Release Induced by Compound 48/80, Bradykinin and a Polyethylenimine in Rat Peritoneal Mast Cells," Jpn. J. Pharmacol., 64: 1-8 (1994).

Trichopoulou, A. et al., "Cancer and Meditarranean Dietary Traditions," Cancer Epidemiology, Biomarkers, & Prevention, vol. 9: 869-873 (Sep. 2000).

Theoharides, T.C., "The Mast Cell: A Neuroimmunoendocrine Master Player," Int. J. Tiss. Reac. XVIII(1), 1-21 (1996).

Theoharides, T.C., "Histamine2 (H2)-Receptor Antagonists in the Treatment of Urticaria," Drugs 37: 345-355 (1989).

Theoharides, T. "Mast Cells and Migraines," Brief Proposal, (1983).

Morrow, J. et al., "Indentification of Skin as a Major Site of Prostaglandin D2 Release Following Oral Administration of Niacin in Human," J. Invest. Derm., vol. 98(5): 812-815 (1992).

Weston, A. et al., "Terminal Ileal Mucosal Mast Cells in Irritable Bowel Syndrome," Dig. Diseases and Sci., vol. 38(9): 1590-1595 (Sep. 1993).

Shapiro, G. et al., "Cromolyn Sodium: A Review," Pharmacotherapy, vol. 5(3): 156-170 (May/Jun. 1985).

Database WPI: 2001-358435—XP002221703, "Compositions comprising hyaluronic acid and flavonoids," (2 pages).

International Search Report issued for PCT/US02/00476, dated Dec. 16, 2002 (6 pages).

Parodi et al., Arch. Psicol. Neurol. Psichiatr. vol. 49(3): 299-303 (1988).

Split et al., "Ketotifen in the Treatment of Chronic Cluster Headache," Headache, vol. 24(30: 147-148: 1984).

Unlisted Drugs, vol. 20(11): 167 (Nov. 1968).

Debeuckelaere, et al., "Systemic Mast Cell Disease: A review of the literature with special focus on the gastrointestinal manifestations", Acta clinica Belgica, 46, 226-232 (1991).

Koblenzer, C.S. "Neurotic excoriations and dermatitis artefacta," Dermatologic Clinics, vol. 14(3): 447-455 (Jul. 1996).

Tauberg, J. et al., "Stress-induced urticaria associated with local anesthetic administration," Anesthesia Progress, vol. 30(6): 199-200 (1983).

Theoharides, T.C. "Mast Cells: The Immune Gate to the Brain," Life Sciences, vol. 46: 607-617 (1990).

Lambracht-Hall, M. et al., "Serotonin Release From Rat Brain Mast Cells In Vitro," Neuroscience, vol. 39(1) 199-207 (1990).

Dimitriadou, V. et al., Histochemical and Ultrastructural Characteristics of Rat Brain Perivascular Mast Cells Stimulated With Compound 48/80 and Carbachol, Neuroscience, vol. 39(1): 209-224 (1990).

Pearce, F.L. "Mast cell heterogeneity," TIPS: 165-167 (Apr. 1983).

Theoharides, T.C. and Douglas, W.W. "Somatostatin Induces Histamine Secretion From Rat Peritoneal Mast Cells," Endocrinology, vol. 102(5): 1637-1640 (Nov. 7, 1977).

Sundaram, K. et al., "Antagonists of luteinizing hormone releasing hormone bind to rat mast cells and induce histamine release," Agents and Actions, vol. 25(3/4): 307-313 (1988).

Prior, A. and Read, N.W. "Reduction of rectal sensitivity and postprandial motility by granisetron, a 5HT3 receptor antagonist, in patients with irritable bowel syndrome (IBS)," Brit. Soc. of Gasteroent., A1174.

Mathias, J. et al., "Debilitating 'Functional' Bowel Disease Controlled by Leuprolide Acetate, Gonadotropin-Releasing Hormone (GnRH) Analog," Digestive Diseases and Sciences, vol. 34(5): 761-766 (May 1989).

Read, N.W. "Irritable bowel syndrome (IBS)—definition and pathophysiology,", vol. 130: 7-13 (1987), Scand. J. Gastroenterol Suppl.

Stefanini, G.F. et al., "Oral disodium cromoglycate treatment on irritable bowel syndrome: An open study on 101 subjects with diarrheic type," vol. 87: 55-57 (1992), Am. J. Gastroenterol.

International Search Report issued for PCT/US95/01392, dated May 31, 1995 (4 pages).

Hendriks, J. et al., "Flavonoids Influence Monocytic CTPase Activity and Are Protective in Experimental Allergic Encephalitis," J. Exp. Med., vol. 200(12): 1667-1672 (2004).

Mezzapesa, D. et al., "Glatiramer acetate in multiple sclerosis," Expert Rev. Neurotherapeutics (5)4: 451-458 (2005).

Gupta, E. et al., "Lovastatin and Extended-Release Niacin Combination Product: The First Drug Combination for the Management of Hyperlipidia," Heart Disease, vol. 4, 124-137 (2002).

Owens, M.J. and Nemeroff, C.B., "Physiology and Pharmacology of Corticotropin-releasing Factor," Pharmacological Reviews, vol. 43(4): 425-615 (1991).

Devlin, Thomas (ed): Textbook of Biochemistry with Clinical Correlations, 2nd Edition: Ch. 8.5-8.6, 345-351 (1982).

Simopoulos, A.P., Visioli F. (eds): Mediterranean Diets. World Rev. Nutr. Diet. Basel, Karger, vol. 87: 56-77 (2000).

Urade, Y. et al., "The Major Source of Endogenous Prostaglandin D2 Production is Likely Antigen-Presenting Cells," J. Immunol., 143(9): 2982-2989 (Nov. 1, 1989).

Lidor, C. et al., "Osteoporosis as the Sole Presentation of Bone Marrow Mastocytosis," J. Bone Min Res., vol. 5(8): 871-876 (1990).

Kimata, M. et al., "Effects of luteolin, quercetin and baicalein on immunoglobulin E-mediated mediator release from human cultured mast cells," Clin. and Exper. Allergy, vol. 30, 501-508 (2000).

Letters to the Editor, J. Allergy Clin. Immunol., vol. 119(2): 498-499 (Oct. 18, 2006).

Irani, A-M, et al., "Mast Cell Changes in Scleroderma," Arth. and Rheuma., vol. 35(8): 933-939 (Aug. 1992).

(56) References Cited

OTHER PUBLICATIONS

Dunn, R.T. et al., "Low-Dose Aspirin and Ibuprofen Reduce the Cutaneous Reactions Following Niacin Administration," Am. J. Thera., 2: 478-480 (1995).

Dvorak, A.M. et al., "Human Gut Mucosal Mast Cell: Ultrastructural Observations and Anatomic Variation in Mast Cell-Nerve Associations in vivo," Int. Archives of Allergy & Immunology, vol. 98: 158-168 (1992).

Cefali, E.A. et al., "Aspirin reduces cutaneous flushing after administration of an optimized extended-release niacin formulations," Int. J. Clin. Pharm. Ther., vol. 45: 78-88 (2007).

Verbeek, R. et al., "Oral flavonoids delay recovery from experimental autoimmune encephalomyelitis in SJL mice," Biochem. Pharm., 70: 220-228 (2005).

Trichopoulou, A. et al., "Diet and Survival of Elderly Greeks: a link to the past1-4." Am. J. Clin. Nutri., vol. 61(suppl.): 1346S-50S (1995).

Tsakalos, N, et al., "Induction of Mast Cell Secretion by Parathormone," Biochemical Pharmacology, vol. 32(2): 355-360 (1983).

Theoharides, T. et al., "Bladder Mast Cell Activation in Interstitial Cystitis," Seminars of Urology, vol. IX(2): 74-87 (May 1991).

Shoskes, D., et al., "Quercetin in men with category III chronic prostatis: a preliminary prospective, double-blind, placebo-controlled trial," Urology, 54(6): 960-963 (1999).

Seibold, J. et al., "Dermal Mast Cell Degranulation in Systemic Sclerosis," Arth. and Rheuma., vol. 33(11): 1702-1709 (Nov. 1990).

Rockoff, S.D. and Armstrong, J.D. "Parathyroid Hormone as a Stimulus to Mast Cell Accumulation in Bone," Calc. Tiss. Res., 5: 49-55 (1970.

Morrow, J.D., et al., "Release of markedly increased quantities of prostaglandin D2 in vivo in humans following the administration of nicotinic acid," Prostaglandins, vol. 38(2): 263-274 (1989).

Boushey, R. et al., "Adrenal Cortical Carcinoma," Curr. Treatment Op. Oncol., 2: 355-364 (2001).

Chines, A. et al., "Systemic Mastocytosis Presenting as Osteoporosis: A Clinical and Histomorphometric Study," J. Clin. Endocrinol. and Metab., vol. 72(1): 140-144 (1991).

Singleton, V.L. and Rossi, J.A. "Colorimetry of Total Phenolics with Phosphomolybdic-Phosphotungstic Acid Reagents," Phenolics Determination, pp. 144-158, Am. J. Enol. Vitic. 16 (3) ; 1965.

Theoharides, T.C. and Doyle, R. "Autism, Gut-Blood-Brain Barrier, and Mast Cells," J. Clin. PsychoPharm, 28(5): 479-483 (2008).

Theoharides, T.C. and Konstantinidou, A.D., "Corticotropin-releasing hormone and the blood-brain-barrier," Frontiers in Bioscience, 12: 1615-1528 (Jan. 1, 2007).

Theoharides, T.C. et al., "Mast cells as targets of corticotrophin-releasing factor and related peptides," Trends in Pharmaco. Sci., vol. 25(11): 563-568 (Nov. 2004).

Jang, S., et al., "Luteolin reduces IL-6 production in microglia by inhibiting JNK phosphorylation and activation of AP-1," PNAS, vol. 105(21): 7534-3539 (May 27, 2008).

Barreau, F. et al., "Pathways involved in gut mucosal barrier dysfunction induced in adult rats by maternal depreviation: corticotrophin-releasing factor and nerve growth factor interplay," J. Physiol., vol. 580(1): 347-356 (2007).

Kinney, D. et al., "Prenatal stress and risk for autism," Neuroscience and Biobehavioral Reviews, 32: 1519-1532 (2008).

Sharma, V. et al., "Modulation of interleukin-1B mediated inflammatory response in human astrocytes by flavonoids: Implications in neuroprotection," Brain Research Bulletin, 73: 55-63 (2007).

Kumar, A. and Goyal, R. "Quercetin Protects Against Acute Immobulization Stress-Induced Behaviors and Biochemical Alterations in Mice," J. Med. Food, 11(3): 469-473 (Sep. 1, 2008).

Theoharides, T. et al., "Novel therapeutic targets for autism," Trends in Pharmaco. Sci., vol. 29(8): 375-382 (2008).

International Search report issued for PCT/US09/52577, mailed on Nov. 24, 2009 (5 pages).

Wesolowski, Autism: Unknown Causes, Known Effects, J. for Pre-Health Affiliated Students, vol. V(1): 19-22 (Winter 2005).

Wing, "Autism Spectrum Disorders" BMJ J. vol. 312: 327-328 (Feb. 10, 1996).

\* cited by examiner

METHODS OF TREATING AUTISM SPECTRUM DISORDERS AND COMPOSITIONS FOR SAME

FIELD OF THE INVENTION

The present disclosure is in the field of medicine. More specifically, this disclosure relates to methods, certain compositions, and the use of those methods and compositions for screening for and treating autistic spectrum disorders.

BACKGROUND

Autism spectrum disorders (ASDs) are pervasive neurodevelopmental disorders diagnosed in early childhood when acquired skills are lost or the acquisition of new skills becomes delayed. ASDs onset in early childhood and are associated with varying degrees of dysfunctional communication and social skills, in addition to repetitive and stereotypic behaviors. In many cases (25%-50%), a period of seemingly normal development drastically shifts directions as acquired skills are lost or the acquisition of new skills becomes delayed.

In recent years, the number of people with an ASD has increased considerably to approximately 1 in 150 children, but it is not clear whether this increase is because of a higher prevalence of the disorder, improved awareness by clinicians, or a combination of both.

A number of studies have reported that patients with ASDs have in their blood antibodies against brain proteins. Brain blood vessels can become leaky (permeable) at some point during a child's development and allow circulating immune cells to be exposed to brain proteins that were mistaken by the immune system as foreign. As a result, antibodies are made against those brain proteins. Such antibodies against brain proteins can disrupt normal brain function and, alone or together with other circulating immune cell-derived destructive molecules, can contribute to brain damage and to the pathogenesis of ASDs. Moreover, increased brain blood vessel leakage can increase intracranial pressure and contribute to macrocephaly reported in many children with ASDs, thus further compromising brain function.

There is currently no explanation for what caused the brain blood vessels to become leaky. Identification of molecules that can make brain blood vessels leak could lead to the development of diagnostic markers. Preventing brain blood vessel leakage in susceptible children, or reversing brain blood vessel leakage in children who have already developed ASDs, could provide a novel therapeutic intervention.

Currently, there are no known defined mechanisms of pathogenesis, diagnostic markers, or curative therapy available for ASDs. An important need therefore exists for methods and compositions that are effective to screen for and treat ASDs. Various embodiments of the invention address these needs.

SUMMARY OF THE INVENTION

It has been discovered that measurement of certain serum markers capable of making brain blood vessels leaky can identify patients with ASDs. It has also been discovered that certain compositions can inhibit leakage of brain vessels that would otherwise allow entry of noxious molecules in the brain. The compositions disclosed herein have been found to improve the conditions associated with ASDs through inhibition of blood vessel leakage, as determined by behavioral improvement and as noted in the examples disclosed herein.

Together, these data support that modulation, and, in particular, inhibition, of brain blood vessel leakage is a valuable intervention point for the treatment of ASDs. This discovery has been exploited to develop the present application, which includes methods and compositions for treating ASDs in a subject, as well as methods for screening for an ASD in a subject suspected of having an ASD.

One aspect of the application is directed to a method of treating an ASD in a subject. In this method, a composition comprising of one or more flavonoids, alone or in combination with, a serotonin blocker, a histamine-1 receptor antagonist, a histamine-3 receptor agonist, an antipsychotic agent, a heavy metal chelator, a neurotensin blocker, olive kernel extract and a physiologically acceptable carrier, is administered to a subject in need thereof, wherein the composition modulates the leakage of brain blood vessels.

In particular embodiments, the composition inhibits brain blood vessel leakage.

In certain embodiments, the ASD is autism.

In other embodiments, the ASD is Asperger's syndrome, Rett syndrome, childhood disintegrative disorder, or atypical autism otherwise known as pervasive developmental disorder not otherwise specified (PDD-NOS).

In particular embodiments, the flavonoid is apigenin, astragaline, (−)-epigallocatechin-3 gallate, genistein, hesperetin, hesperidin, kaempferol, luteolin, myricetin, quercetin, or rutin.

In yet other embodiments, the serotonin blocker is the serotonin receptor antagonist azatadine or cyproheptadine.

In yet other embodiments, the histamine-1 receptor antagonist is azatadine, azelastine, cyproheptadine, hydroxyzine, merelastine, or rupatadine.

In additional embodiments, the histamine-3 receptor agonist is R(−)-α-methyl histamine, $N^\alpha$-methyl histamine, $N^\tau$-methyl histamine, α-$N^\alpha$-dethylhistamine, α,β-dimethyl histamine, $N^\alpha$-methyl-α-(dimethyl)histamine, $N^\alpha$-methyl-α-(chloromethyl)histamine, or α,β-difluoro-$N^\alpha$-(fluoromethyl)histamine.

In some embodiments, the neurotensin blocker is SR48692, SR 142948A (Sanofi-Aventis, Paris, France).

In other embodiments, the antipsychotic agent is risperidone.

In certain embodiments, the heavy metal chelator is meso-2,3-dimercaptosuccinic acid (DMSA).

Another aspect of the application is directed to a method of inhibiting brain blood vessel leakage in a subject. In this method, a composition comprising one or more flavonoids, alone or in combination with, a serotonin blocker, a histamine-1 receptor antagonist, a histamine-3 receptor agonist, an antipsychotic agent, a neurotensin blocker, a heavy metal chelator, olive kernel extract and a physiologically acceptable carrier, is administered to a subject in need thereof, wherein the composition modulates the leakage of brain blood vessels.

In particular embodiments, the flavonoid is apigenin, astragaline, (−)-epigallocatechin-3 gallate, genistein, hesperetin, hesperidin, kaempferol, luteolin, myricetin, quercetin, or rutin.

In other embodiments, the serotonin blocker is azatadine or cyproheptadine.

In yet other embodiments, histamine-1 receptor antagonist is azatadine, azelastine, cyproheptadine, hydroxyzine, merelastine, or rupatadine.

In additional embodiments, the histamine-3 receptor agonist is R(−)-α-methyl histamine, $N^\alpha$-methyl histamine, $N^\tau$-methyl histamine, α-$N^\alpha$-dethylhistamine, α,β-dimethyl histamine, N$^\alpha$-methyl-α-(dimethyl)histamine, N$^\alpha$-methyl-α-(chloromethyl)histamine, or α,β-difluoro-N$^\alpha$-(fluoromethyl)histamine.

In some embodiments, the neurotensin blocker is SR48692, SR 142948A (Sanofi-Aventis, Paris, France).

In other embodiments, the antipsychotic agent is risperidone.

In other embodiments, the heavy metal chelator is meso-2,3-dimercaptosuccinic acid (DMSA).

Yet a further aspect of the application is directed to a method of screening a subject to determine whether the subject has an ASD. The method comprises collecting blood serum from a subject suspected of having an ASD. Next, the serum sample is assayed for the level of a certain marker or markers. Finally, the level of marker or markers is compared against the level of the same marker or markers from a subject known not to have an ASD. A higher level of the marker in a subject suspected of having an ASD indicates that the subject may have an ASD.

In some embodiments, the markers are neurotensin (NT) and/or interleukin-6 (IL-6). In other embodiments, the markers are interleukin-33 (IL-33), platelet activating factor (PAF), tryptase and vascular endothelial growth factor (VEGF).

In other embodiments, these markers may be expressed at higher levels and produced by peripheral blood lymphocytes with or without stimulation by triggers such as phytohemagglutinin (PHA), or NT, or specific anti-brain antibodies. In yet other embodiments, higher levels of these markers may be identified in the cerebrospinal fluid (CSF).

In an additional aspect of the application, a composition for treating an ASD is provided. The composition comprises one or more flavonoids, alone or in combination with, a histamine-1 receptor antagonist, a histamine-3 receptor agonist, a serotonin blocker, an antipsychotic agent, a neurotensin blocker, a heavy metal chelator, olive kernel extract and a physiologically acceptable carrier. The composition modulates the leakage of brain blood vessels.

Another aspect of the application is directed to a kit to treat a subject with an ASD. The kit comprises at least one dosage of a composition comprising one or more flavonoids, alone or in combination with a histamine-1 receptor antagonist, a histamine-3 receptor agonist, a serotonin blocker, an antipsychotic agent, a neurotensin blocker, a heavy metal chelator, olive kernel extract and a physiologically acceptable carrier for administration to the subject.

In some embodiments, the dosage is in a container, which can be sterile, containing an effective dose of the composition and a physiologically acceptable vehicle. The kit can further comprise a label or instructions to treat a subject with an ASD with the composition.

A further aspect of the application is directed to a kit to screen a biological sample for an ASD. The kit comprises of a rapid assay for blood levels of NT and IL-6.

In some embodiments, the dosage is in a container, which can be sterile and can sample the blood directly from the subject in question by self-administration. The kit can further comprise a label or instructions to screen a biological sample for an ASD with the composition.

DESCRIPTION

This application relates to methods and compositions for inhibiting brain blood vessel leakage, methods and compositions for screening for and treating autism spectrum disorders, and to pharmaceutical compositions comprising these compositions.

Throughout this application, various patents, patent applications and publications are referenced. The disclosures of these patents, patent applications, and publications in their entireties are incorporated into this application by reference in order to more fully describe the state of the art as known to those skilled therein as of the date of this application. This disclosure will govern in the instance that there is any inconsistency between the patents, patent applications and publications and this disclosure.

DEFINITIONS

The articles "a" and "an" are used in this disclosure to refer to one or more than one (i.e., to at least one) of the grammatical object of the article. By way of example, "an element" means one element or more than one element.

The term "or" is used in this disclosure to mean, and is used interchangeably with, the term "and/or," unless indicated otherwise.

The term "about" is used in this disclosure to mean a value − or +20% of a given numerical value. Thus, "about 60%" means a value between 60-20% of 60 and 60+20% of 60 (i.e., between 48% and 72%).

The terms "autism spectrum disorder" and "ASD" or "ASDs" are used in this disclosure to refer to a spectrum of disorders characterized by abnormalities of social interactions and communication, as well as restricted interests and repetitive behavior. This spectrum includes, but is not limited to, autistic disorder, Asperger's syndrome, childhood disintegrative disorder, and atypical autism or pervasive developmental disorder not otherwise specified (PPD-NOS), as well as Rett syndrome and tuberous sclerosis.

The term "carrier" is used in this disclosure to encompass carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "composition" is used in this disclosure to mean a combination or mixture of one or more substances.

The terms "effective amount" and "therapeutically effective amount" are used in this disclosure to refer to an amount of a composition that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The phrase "pharmaceutically acceptable" is used in this disclosure to refer to compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "subject" is used in this disclosure to include, without limitation, a human or an animal. Exemplary animals include, but are not limited to, mammals such as mouse, rat, guinea pig, dog, cat, horse, cow, pig, monkey, chimpanzee, baboon, or rhesus monkey.

"Synergistic" is used in this disclosure to mean "coordinated or correlated action by two or more structures or drugs" [*Stedman's Medical Dictionary*, 23rd edition, Williams & Wilkins, Baltimore, 1976].

The term "treating" is used in this disclosure to mean the reduction or amelioration of at least one symptom of any disorder to any extent, and includes, but does not require, a complete cure of the disorder. Treating can be curing, improving, or partially ameliorating a disorder.

"Brain blood vessel leakage" is used in this disclosure to mean leakage from blood vessels, especially as they pertain to the brain, otherwise referred to as increased vascular permeability.

The terms "screen", "screen for", and "diagnose" are used interchangeably in this disclosure.

The term "blocker" is used to mean inhibition, prevention, neutralization, or amelioration of the particular molecules to which it refers. "Blocker" includes, but is not limited to, use of an antagonist, an antibody, a soluble receptor, a receptor variant, or any other inhibitor.

The following abbreviations are used in this disclosure and having the following definitions: Aberrant Behavior Checklist is abbreviated as "ABC"; interleukin-6 and interleukin-33 are abbreviated "IL-6" and "IL-33", respectively; neurotensin is abbreviated as "NT"; platelet activating factor is abbreviated as "PAF"; phytohemagglutinin is abbreviated as "HPA"; vascular endothelial growth factor is abbreviated as "VEGF"; minute or minutes is abbreviated "min".

Compositions

Aberrant, or immature development, or disruption of the integrity of brain blood vessels exposes the brain to noxious molecules that can adversely affect its function. Such exposure can contribute to or lead to the development of ASDs. Blood from children with ASDs often contains a number of autoantibodies against brain peptides indicating that there must have been increased brain blood vessel vascular permeability at some point in order for immune cells to enter the brain and produce antibodies against certain brain proteins.

It has been discovered that a composition comprising one or more flavonoids, alone or in combination with a histamine-1 receptor antagonist, a histamine-3 receptor agonist, a serotonin blocker, an antipsychotic agent, a neurotensin blocker, a heavy metal chelator, olive kernel extract and a physiologically acceptable carrier have synergistic effects when used, without or with a conventional clinical treatment, to treat ASDs. The olive kernel extract alone may be used to improve the transmembrane transport of difficult-to-absorb biomolecules in the brain.

In certain embodiments, the autism spectrum disorder is autism.

In other embodiments, the autism spectrum disorder is Asperger's syndrome, Rett syndrome, childhood disintegrative disorder, or pervasive developmental disorder not otherwise specified (PPD-NOS).

In particular embodiments, the flavonoid is apigenin, astragaline, (−)-epigallocatechin-3 gallate, genistein, hesperetin, hesperidin, kaempferol, luteolin, myricetin, quercetin, or rutin.

In yet other embodiments, histamine-1 receptor antagonist is azatadine, azelastine, cyproheptadine, hydroxyzine, merelastine, or rupatadine.

In additional embodiments, the histamine-3 receptor agonist is $R(-)$-$\alpha$-methyl histamine, $N^\alpha$-methyl histamine, $N^\alpha$-methyl histamine, $\alpha$-$N^\alpha$-dethylhistamine, $\alpha,\beta$-dimethyl histamine, $N^\alpha$-methyl-$\alpha$-(dimethyl)histamine, $N^\alpha$-methyl-$\alpha$-(chloromethyl)histamine, or $\alpha,\beta$-difluoro-$N^\alpha$-(fluoromethyl)histamine.

In some embodiments, the serotonin blocker is cyproheptadine.

In some embodiments, the neurotensin blocker is SR48692, SR 142948A (Sanofi-Aventis, Paris, France).

In other embodiments, the antipsychotic agent is risperidone.

In some embodiment, the heavy metal chelator is meso-2,3-dimercaptosuccinic acid (DMSA).

The olive kernel extract component is described in U.S. Publication No. 2006/0013905, which is fully incorporated into this application by reference.

Methods of Treating

A composition of this disclosure is useful to treat an ASD by inhibiting brain blood vessel leakage. When administered to a subject with an ASD, the disclosed compositions, or therapeutic formulations containing such compositions, modulate at least one behavioral symptom of the disorder being treated. A physician with training in the diagnosis and treatment of the relevant ASD disorder will be able to detect the modulation in the at least one symptom of the relevant disorder. One of the screening tests for such improvement is the Aberrant Behavior Checklist (ABC).

This disclosure is also directed to kits to screen for an ASD in a subject. A kit comprises at least a rapid way of obtaining a blood sample and screening for increased levels of NT and IL-6 in the subject. The container can be sterile, permitting a sufficient amount of blood to be drawn into a physiologically acceptable vehicle for immediate or further analysis. The kit can also include a label or instructions to screen for an ASD in a subject.

Although not bound by any particular mechanism of action of the components of the claimed compositions, the inventor contemplates that they inhibit brain blood vessel leakage.

Methods of Screening

This application is also directed to methods of screening a subject to determine whether the subject has an ASD. The method comprises collecting blood from a subject suspected of having an ASD. Next, the serum or plasma is separated from the sample is assayed for the level of a certain marker or markers. The expression and/or production of the markers can also be identified in peripheral blood leukocytes from the blood plasma either before or after stimulation with such triggers as phytohemasgglutinin (HPA) or NT in vitro. The marker or markers can be, for example, NT, IL-6, IL-33, PAF, and VEGF. Finally, the level of the marker or markers are compared against the level from a subject known not to have an ASD. A higher level of the marker in a subject suspected of having an ASD indicates that the subject may have an ASD.

The levels of the markers can be measured by various assays. For example, the levels of neurotensin and IL-6 can be measured by commercially available ELISA kits (e.g. R & D Systems, Indianapolis, Ind.) or by multiplex microbead arrays (e.g., Millipore, Billerica, Mass.). Other methods include intradermal blood sampling and electrochemical detection of some of the markers.

Formulation

This disclosure is also directed to a pharmaceutical formulation comprising at least one disclosed composition, and a pharmaceutically-acceptable carrier. Such formulations are suitable for administration to a subject. The pharmaceutical formulation can be used for treating a disorder described above.

Any suitable pharmaceutically acceptable carrier known in the art can be used as long as it does not affect the inhibitory activity of a disclosed composition. Carriers may be used that efficiently solubilize the agents. Carriers include, but are not limited to, a solid, liquid, or a mixture of a solid and a liquid. The carriers can take the form of capsules, tablets, pills, powders, lozenges, suspensions, emulsions, or syrups. The carriers can include substances that act as flavoring agents, lubricants, solubilizers, suspending agents, binders, stabilizers, tablet disintegrating agents, and encapsulating materials. Other examples of suitable physiologically acceptable carriers are described in *Remington's Pharmaceutical Sciences* (21st ed. 2005), incorporated into this disclosure by reference.

Non-limiting examples of materials which can serve as pharmaceutically-acceptable carriers include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline, (18) Ringer's solution, (19) ethyl alcohol; (20) phosphate buffer solutions; and (21) other non-toxic compatible substances employed in pharmaceutical formulations.

The formulations can conveniently be presented in unit dosage form and can be prepared by any methods known in the art of pharmacy. The amount of a disclosed composition that can be combined with a carrier material to produce a single-dosage form will vary depending upon the subject being treated, the particular mode of administration, the particular condition being treated, and other considerations. The amount of a disclosed composition that can be combined with a carrier material to produce a single-dosage form will generally be that amount of the composition that produces a therapeutic effect. Generally, out of one hundred percent, this amount will range from about 1 percent to about ninety-nine percent of active ingredient, in some instances from about 5 percent to about 70 percent, in other instances from about 10 percent to about 50 percent.

Methods of preparing these formulations or compositions include the step of bringing into association a composition disclosed in this application with a carrier and, optionally, one or more accessory ingredients. In general, the formulations are prepared by uniformly and intimately bringing into association a composition of this disclosure with liquid carriers, or timely divided solid carriers, or both, and then, if necessary, shaping the product.

In solid dosage forms of the disclosed compositions for oral administration (e.g., capsules, tablets, pills, dragees, powders, granules, and the like), the active ingredient is mixed with one or more additional ingredients, such as sodium citrate or dicalcium phosphate, and/or any of the following: (1) fillers or extenders, such as, but not limited to, starches, lactose, sucrose, glucose, mannitol, and/or silicic acid; (2) binders, such as, but not limited to, carboxymethylcellulose, alginates, gelatin, polyvinyl pyrrolidone, sucrose, and/or acacia; (3) humectants, such as, but not limited to, glycerol; (4) disintegrating agents, such as, but not limited to, agar, calcium carbonate, potato or tapioca starch, alginic acid, certain silicates, and sodium carbonate; (5) solution retarding agents, such as, but not limited to, paraffin; (6) absorption accelerators, such as, but not limited to, quaternary ammonium compounds; (7) wetting agents, such as, but not limited to, cetyl alcohol and glycerol monostearate; (8) absorbents, such as, but not limited to, kaolin and bentonite clay; (9) lubricants, such as, but not limited to, talc, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols, and the like.

In powders, the carrier is a finely-divided solid, which is mixed with an effective amount of a finely-divided agent. Powders and sprays can contain, in addition to a composition of this disclosure, excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Tablets for systemic oral administration can include one or more excipients as known in the art, such as, for example, calcium carbonate, sodium carbonate, sugars (e.g., lactose, sucrose, mannitol, sorbitol), celluloses (e.g., methyl cellulose, sodium carboxymethyl cellulose), gums (e.g., arabic, tragacanth), together with one or more disintegrating agents (e.g., maize, starch, or alginic acid, binding agents, such as, for example, gelatin, collagen, or acacia), lubricating agents (e.g., magnesium stearate, stearic acid, or talc), inert diluents, preservatives, disintegrants (e.g., sodium starch glycolate), surface-active and/or dispersing agent. A tablet can be made by compression or molding, optionally with one or more accessory ingredients.

In solutions, suspensions, emulsions or syrups, an effective amount of a disclosed composition is dissolved or suspended in a carrier, such as sterile water or an organic solvent, such as aqueous propylene glycol. Other formulations can be made by dispersing the agent in an aqueous starch or sodium carboxymethyl cellulose solution or a suitable oil known to the art. The liquid dosage forms can contain inert diluents commonly used in the art, such as, for example, water or other solvents, solubilizing agents and emulsifiers, such as, but not limited to, ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols, and fatty acid esters of sorbitan, and mixtures thereof.

Besides inert diluents, the oral formulations can also include adjuvants, such as wetting agents, emulsifying and suspending agents, sweetening, flavoring, coloring, perfuming, and preservative agents.

Suspensions can contain, in addition to the disclosed composition, suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Formulations of the pharmaceutical compositions for rectal or vaginal administration can be presented as a suppository, which can be prepared by mixing one or more compositions of this disclosure with one or more suitable non-irritating excipients or carriers comprising, for example, cocoa butter, polyethylene glycol, a suppository wax or a salicylate, and which is solid at room temperature but liquid at body temperature and, thus, will melt in the rectum or vaginal cavity and release the agents. Formulations suitable for vaginal administration also include, but are not limited to, pessaries, tampons, creams, gels, pastes, foams, or spray formulations containing such carriers as are known in the art to be appropriate.

Dosage forms for the topical or transdermal administration of a composition of this disclosure include, but are not limited to, powders, sprays, ointments, pastes, creams, lotions, gels, solutions, patches, and inhalants. The disclosed composition can be mixed under sterile conditions with a pharmaceutically-acceptable carrier, and with any preservatives, buffers, or propellants.

Ointments, pastes, creams, and gels can contain, in addition to a disclosed composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a composition of this disclosure to the body. Such dosage forms can be made by dissolving or dispersing the agents in the proper medium. Absorption enhancers can also be used to increase the flux of the agents across the skin. The rate of such flux can be controlled by either providing a rate controlling membrane or dispersing the subject composition in a polymer matrix or gel.

The compositions of this application are administered in a therapeutically effective amount to a patient in need of such treatment. This amount can vary, depending on the activity of the agent utilized, the nature of the disorder, and the health of the patient, among other considerations. A skilled practitioner will appreciate that the therapeutically effective amount of a disclosed composition can be lowered or increased by fine-tuning and/or by administering more than one disclosed composition, or by administering a composition of this disclosure together with a second agent (e.g., antibiotics, antifungals, antivirals, NSAIDS, DMARDS, steroids, etc.). Therapeutically effective amounts can be easily determined, for example, empirically by starting at relatively low amounts and by step-wise increments with concurrent evaluation of beneficial effect (e.g., reduction in symptoms). The actual effective amount will be established by dose/response assays using methods standard in the art (Johnson et al., *Diabetes*, (1993) 42:1179). As is known to those in the art, the effective amount will depend on bioavailability, bioactivity, and biodegradability of the composition of this application.

The concentration range of the flavonoids of the oral formulations can be 10-3,000 mg per tablet or capsule. Generally, where present, the amounts of the unrefined olive kernel extract is about 30-50% of the other active ingredients and can be 300-1200 mg. The number of capsules or tablets to be taken per day is determined by the nature and severity of the medical condition, and is readily determinable by the patient's health provider. Other representative formulations are described in the examples below.

The therapeutically effective amount will vary with the subject being treated. Administration of the composition of this disclosure can be hourly, daily, weekly, monthly, yearly, or a single event. For example, the effective amount of the composition can comprise from about 20 mg/kg body weight to about 500 mg/kg body weight and the tablets or capsules can be administered as 2-4/20 kg body weight. When one or more compositions or agents are combined with a carrier, they can be present in an amount of about 1 weight percent to about 99 weight percent, the remainder being composed of the pharmaceutically-acceptable carrier.

Administration

Methods of administration of the therapeutic formulations comprising the compositions of this disclosure can be by any of a number of methods known in the art. These methods include, but are not limited to, local or systemic administration. Exemplary routes of administration include, but are not limited to, oral, parenteral, transdermal, intradermal, intramuscular, intraperitoneal, intravenous, subcutaneous, intranasal (e.g., nebulizer, inhaler, aerosol dispenser), colorectal, rectal, intravaginal, and any combinations thereof. In addition, it may be desirable to introduce pharmaceutical compositions of the disclosed compositions into the central nervous system by any suitable route, including intraventricular and intrathecal injection. Intraventricular injection can be facilitated by an intraventricular catheter, for example, attached to a reservoir, such as an Ommaya reservoir. Methods of introduction can be provided by rechargeable or biodegradable devices, e.g., depots.

Administration can occur by coating a device, implant, stent, or prosthetic. The compositions of this application can also be used to coat catheters in any situation where catheters are inserted in the body. The compositions of this disclosure may also be used as coatings on implanted medical devices. The coated devices can be used to deliver the disclosed compositions to a subject and to treat or protect against inflammation caused by the device itself. Such medical devices include artificial skins (scaffolding such as naturally occurring polymers, e.g., collagen; man-made polymers, e.g., PTFE, Dacron, PET or polyethylene; self-degrading man-made polymers, e.g., PLA or PGA; biopolymer matrices from animal tissues including fetal and neonatal tissues to be used as tissue engineering scaffolds (cf. Bell et al., U.S. Pat. No. 6,696,074)), artificial joints, band-aids, stents for blood vessels, artificial blood vessels, pacemakers, stents for abdominal support in hernia repair, tissue transplants, prostheses, breast implants, etc. Particularly useful in this regard are compositions containing olive kernel extract in softgel capsules or other appropriate vehicles.

The therapeutic formulations containing a disclosed composition can also be administered as part of a combinatorial therapy with other agents. Combination therapy refers to any form of administration combining two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compositions can be administered either in the same formulation or in a separate formulation, either simultaneously or sequentially. Thus, an individual who receives such treatment can have a combined (conjoint) effect of different therapeutic compositions.

Other therapeutic agents useful potentially useful in ASDs include antioxidants. Antioxidants can be natural or synthetic. Antioxidants are, for example, superoxide dismutase (SOD), 21-aminosteroids/aminochromans, glutathione, S-adenosyl methionine, vitamin C or vitamin E. Many other antioxidants are known to those of skill in the art. The compositions of this application can serve as part of a treatment regimen that may combine many different anti-inflammatory agents. For example, the subject compositions can be administered in combination with one or more of an NSAID, DMARD, or immunosuppressant.

The disclosure is further illustrated by the following examples, which are not to be construed as limiting this disclosure in scope or spirit to the specific procedures described in this disclosure. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

EXAMPLES

Example 1

Increased Serum Biomarkers in Autism

Figure 1:
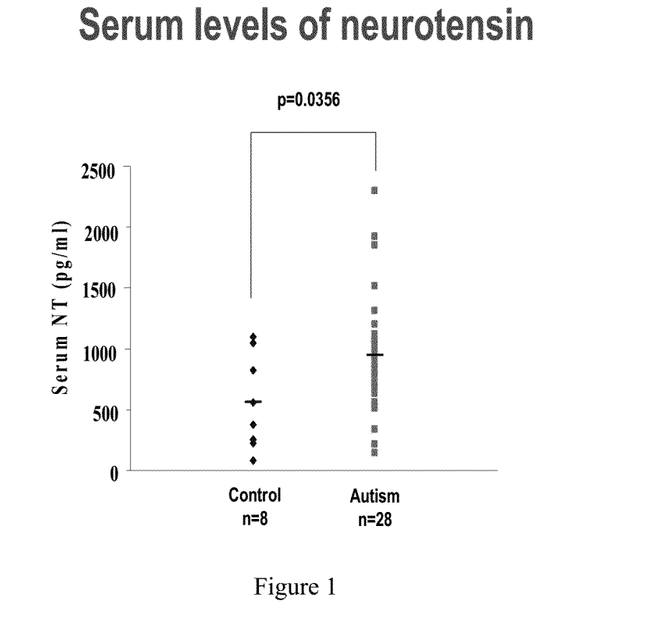
FIG. 1 is a graphic representation of data showing serum levels of neurotensin (NT) of individual patients (2-4 years old with autism) and age-matched normally developing control patients. The data indicate that there is a statistically significant NT increase in children with autism.
Figure 2:
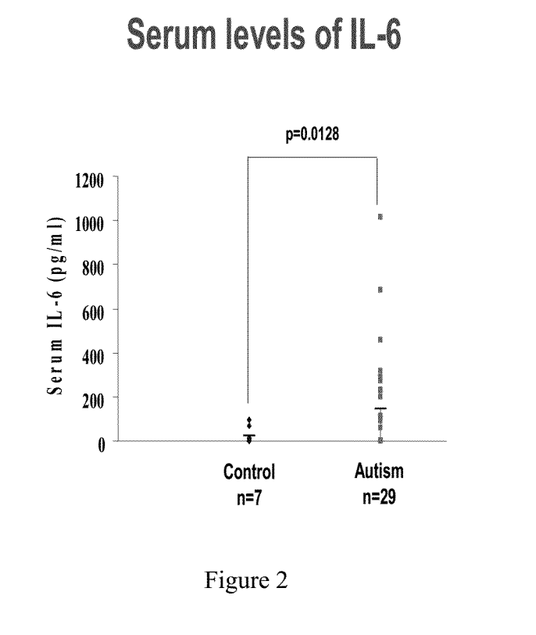
FIG. 2 is a graphic representation of data showing serum levels of interleukin-6 (IL-6) of individual patients (2-4 years old with autism) and age-matched normally developing control patients. That data indicate that there is a statistically significant IL-6 increase in children with autism.

Serum was collected from white, non-Latino healthy subjects (n=7, age: 2.5-4 years old) and children with autism (n=29, age: 2.5-3.5 years old) and analyzed for the following peptides: β-endorphin, NT, and substance P (SP), as well as the following cytokines: IL-1α, IL-1β, IL-4, IL-6, IL-8, IL-10, IL-13, using multiplex microbead arrays (Millipore, MA). As shown in FIGS. 1 and 2, only NT and IL-6 showed a statistically significant increase in children with autism as compared to normally developing controls. Thus, both of these molecules could serve as diagnostic markers for ASDs.

Example 2

Inhibitory Effect of Flavonoids on Brain Blood Vessel Leakage

Male BALB/6 mice (6 weeks old, Jackson Laboratories, Bar Harbor, Me.) were injected in their tail vein with 0.2 ml of Evans blue (0.4%). Binding of Evans blue to the albumin found in the blood prevents Evans blue from escaping the circulation and constitutes a good marker from extravasation in brain parenchyma.

Figure 3:
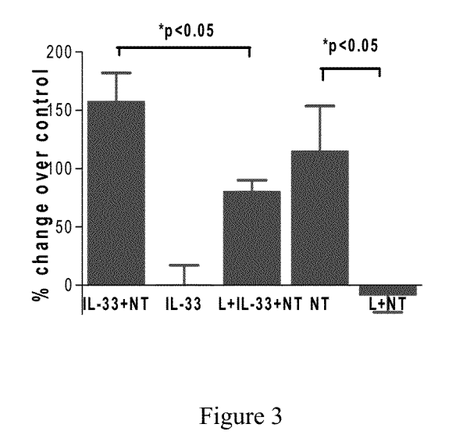
FIG. 3 is a graphic representation of data that shows that intraperitoneal injection of intereleukin-33 (IL-33) together with neurotensin (NT) induced a statistically significant synergistic increase in brain blood vessel leakage in mice, while pretreatment with intraperitoneal injection of luteolin 10 min prior to injection of IL-33 plus NT inhibited brain blood vessel leakage.

Brain blood vessel leakage was assessed with Evans blue extravasation at 2 hr following Evans blue and 30 min after intraperitoneal injection of NT. Mice were anesthetized with a single intraperitoneal injection of ketamine/xylazine (10 mg/kg and 80 mg/kg body weight, each), an intracardiac catheter was inserted in the left ventricle, blood was withdrawn, and 10 ml normal saline was administered intracardially to wash any Evans blue from the systemic circulation. The mice were then decapitated and the whole brain was removed. For brain extravasated Evans blue measurements, the brains were first weighed and the Evans blue was then extracted in 1 ml of N,N-dimethylformamide overnight at 55° C. and the optical density was measured at 620 nm using a PerkinElmer Luminescence Spectrophotometer (Perkin Elmer, Norwalk, Conn.). EB concentration was calculated using a standard curve and values were normalized to the tissue weight and expressed as arbitrary units/mg of tissue. Five animals per group were estimated to be sufficient for significant differences given the variability (<50%) observed. Results of Evans blue/mg tissue were expressed as mean±SD of percent change from control. This statistical analysis was chosen because it permits the experimental results to be compared to their own control and avoids variability from experiment to experiment. Values were then compared using the non-parametric Mann-Whitney U test. Significance is denoted by $p<0.05$. In order to induce brain blood vessel leakage, the mice were either treated only with an intraperitoneal injection (0.5 ml) of NT (500 nmol/kg body weight) or first pretreated with the flavonoid luteolin (40 mg/kg body weight) mixed in olive kernel extract to permit solubilization and increased absorption of the lipid-soluble luteolin. The mice not treated with luteolin were pretreated the same way only with the vehicle in order to keep the conditions similar [olive kernel extract, obtained from Minerva Edible Oils, Athens, Greece (http://www.minerva.com.gr/)]. As shown in FIG. 3, NT induced 150% increase in brain blood vessel leakage, while pretreatment with luteolin completely inhibited brain blood vessel leakage. When the mice were treated with both IL-33 (1 microg/mouse) and NT, brain leakage was even greater (FIG. 3); IL-33 alone had no effect. Pretreatment with the same amount of luteolin as before inhibited brain blood vessel leakage by 50% (FIG. 3). Using more luteolin could inhibit the synergistic effect of IL-33 and NT.

Example 3

NeuroProtek®

NeuroProtek® contains (Table 1) the quercetin glycoside rutin that gets cleaved by intestinal bacteria and acts primarily on the gut. Quercetin is metabolized as "decoy" and allows higher absorption of the lipophilic flavone luteolin. Increased absorption of luteolin is further achieved by formulation in olive kernel extract that forms liposomes that increase absorption.

Quercetin at 10 μM was sufficient to inhibit mast cells by 80%. The amount of 10 μM is 10 mg per 1 liter=1 kg, or 200 mg per 20 kg body weight, assuming that our body is one compartment with equal distribution and complete absorption. If we were to further assume maximal 30% absorption of the flavonoids, then administration is 3×200=600 mg/20 kg body weight. Each NeuroProtek® capsule contains a total of 300 mg flavonoids (Table 1). Thus, two capsules will deliver the required 600 mg/20 kg body weight.

The specific flavonoids proposed are safe. (Harwood M, Danielewska-Nikiel B, Borzelleca J F, Flamm G W, Williams G M, Lines T C. A critical review of the data related to the safety of quercetin and lack of evidence of in vivo toxicity, including lack of genotoxic/carcinogenic properties. *Food Chem Toxicol.* 2007 November; 45(11):2179-205).

Preferred sources of the select flavonoids can be from Pharma Science Nutrients, Inc., Ocala, Fla., while this formulation can be made by GMP-Certified Tishcon Corp., Salisbury, Md.).

TABLE 1

The composition of NeuroProtek ®

| Ingredient | Chemical entity | Source | Purity | Amount (mg/dose) |
|---|---|---|---|---|
| Luteolin | Flavone | Chamomile | 97% | 30 |
| Quercetin | Flavonol | Chamomile | 99% | 170 |
| Rutin | Flavonoid glycoside | Saphora plant | 99% | 100 |
| Olive kernel extract | Oil | Olive seeds | 99% | 40% weight/weight |

Example 4

Effectiveness of NeuroProtek® on Children with Autism

Diagnosis of the specific subjects was made using the Autism Diagnostic Observation Schedule-Generic (ADOS-G, a patient observational tool); follow-up was performed with the ABC screening test. The first subject was an 8 year old boy with Autism and a rash that had never been diagnosed. He had diarrhea when his skin flared up. He had been to allergists and dermatologists for years; they believed he is not allergic. The child was given 2 capsules of NeuroProtek®/20 kg body weight per day. Six months later his behavior improved significantly in that he was as easily excitable and did not purposely repeat arm gestures as before. He was more patient and managed to put letter blocks together to form words.

A 5 year old girl with Atypical Autism (PDD-NOS) would not allow the health provider to even come close to her. She would hide under the table and would scream if addressed more than once. She was put on 2 capsules of NeuroProtek®/20 kg body weight per day. Six months later, her ability to interact with others and learn simple words improved significantly. She would allow the health provider to hold her and help her make simple drawings.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

The invention claimed is:

1. A method of treating an autism spectrum disorder, comprising administering to a subject in need thereof an effective amount of a composition comprising one or more flavonoids, wherein the one or more flavonoids are present in an amount of 10-3,000 mg per tablet or capsule and the flavonoids comprise luteolin, and optionally, a serotonin blocker, a histamine-1 receptor antagonist, a histamine-3 receptor agonist, an antipsychotic agent, a heavy metal chelator, and olive kernel extract and, wherein the composition inhibits brain blood vessel leakage.

2. The method of claim 1, wherein the autism spectrum disorder is autism.

3. The method of claim 1, wherein the autism spectrum disorder is Asperger's disorder.

4. The method of claim 1, wherein the autism spectrum disorder is Rett syndrome.

5. The method of claim 1, wherein one of the one or more flavonoids is apigenin, astragaline, (−)-epigallocatechin-3 gallate, genistein, hesperetin, hesperidin, kaempferol, myricetin, quercetin, or rutin.

6. The method of claim 1, wherein the serotonin blocker is azatadine or cyproheptadine.

7. The method of claim 1, wherein the histamine-1 receptor antagonist is azelastine, azatadine, hydroxyzine, merelastine, or rupatadine.

8. The method of claim 1, wherein the histamine-3 receptor agonist is R(−)-$\alpha$-methyl histamine, $N^{\alpha}$-methyl histamine, $N^{\tau}$-methyl histamine, $\alpha$-$N^{\alpha}$-dethylhistamine, $\alpha,\beta$-dimethyl histamine, $N^{\alpha}$-methyl-$\alpha$-(dimethyl)histamine, $N^{\alpha}$-methyl-$\alpha$-(chloromethyl)histamine, or $\alpha,\beta$-difluoro-$N^{\alpha}$-(fluoromethyl)histamine.

9. The method of claim 1 wherein the antipsychotic agent is risperidone.

10. The method of claim 1 wherein the heavy metal chelator is meso-2,3-dimercaptosuccinic acid.

11. The method of claim 1, wherein the composition is administered by oral or parenteral routes.

12. A method of treating an autism spectrum disorder, comprising administering to a subject in need thereof an effective amount of a composition comprising one or more flavonoids, wherein the one or more flavonoids are present in an amount of 10-3,000 mg per tablet or capsule and the flavonoids comprise luteolin and optionally, a serotonin blocker, a histamine-1 receptor antagonist, a histamine-3 receptor agonist, an antipsychotic agent, a heavy metal chelator, and olive kernel extract.

13. The method of claim 12, wherein the autism spectrum disorder is autism.

14. The method of claim 12, wherein the composition further comprises one or more of apigenin, astragaline, (−)-epigallocatechin-3 gallate, genistein, hesperetin, hesperidin, kaempferol, or myricetin.

15. The method of claim 12, wherein the composition inhibits brain blood vessel leakage.

* * * * *